(12) United States Patent
Díáz-Santiago

(10) Patent No.: US 10,744,045 B2
(45) Date of Patent: Aug. 18, 2020

(54) FEMININE HYGIENE KIT

(71) Applicant: George L. Díáz-Santiago, Bayamón, PR (US)

(72) Inventor: George L. Díáz-Santiago, Bayamón, PR (US)

(*) Notice: Subject to any disclaimer, the term of this patent is extended or adjusted under 35 U.S.C. 154(b) by 670 days.

(21) Appl. No.: 14/041,700

(22) Filed: Sep. 30, 2013

(65) Prior Publication Data
US 2015/0090629 A1   Apr. 2, 2015

(51) Int. Cl.
*B65D 69/00* (2006.01)
*B65D 53/02* (2006.01)
*A61F 13/15* (2006.01)
*B65B 63/02* (2006.01)
*A61F 13/551* (2006.01)
*B65D 71/08* (2006.01)
*B65D 71/10* (2006.01)

(52) U.S. Cl.
CPC .... *A61F 13/5519* (2013.01); *A61F 13/55145* (2013.01); *B65D 71/08* (2013.01); *B65D 71/10* (2013.01)

(58) Field of Classification Search
CPC ........ B65D 69/00; B65D 71/08; B65D 71/10; B65D 71/12; A61F 13/15; A61F 13/55145; A61F 13/5519
See application file for complete search history.

(56) References Cited

U.S. PATENT DOCUMENTS

| | | | |
|---|---|---|---|
| 2,834,459 A * | 5/1958 | Rickard et al. | 206/440 |
| 5,065,868 A * | 11/1991 | Cornelissen et al. | 206/494 |
| 7,104,977 B2 * | 9/2006 | Price et al. | 206/581 |
| 8,342,333 B2 * | 1/2013 | Snell | A61F 13/15747 206/494 |
| 8,944,252 B2 * | 2/2015 | Snell | 206/581 |
| 2003/0070396 A1 * | 4/2003 | Lam et al. | 53/429 |
| 2003/0136704 A1 * | 7/2003 | Burgess | 206/581 |

* cited by examiner

*Primary Examiner* — Andrew D Perreault
(74) *Attorney, Agent, or Firm* — Eugene J. Torres-Oyola; Victor M. Rodriguez-Reyes; Ferraiuoli LLC

(57) ABSTRACT

A compacted feminine hygiene kit comprising basic items such as at least underwear, at least a feminine wipes and at least a feminine sanitary towel. Further the compacted feminine hygiene kit comprises a shaped base for keeping the feminine hygiene kit assembly rigid body while providing a kit, easy to carry, that offers a greater degree of discretion, convenience, and portability to females.

6 Claims, 6 Drawing Sheets

FEMININE HYGIENE KIT

STATEMENT REGARDING FEDERALLY SPONSORED RESEARCH AND DEVELOPMENT

N/A

RELATED APPLICATIONS

N/A

BACKGROUND OF THE DISCLOSURE

Field of the Disclosure

The present disclosure relates to feminine hygiene kits. More particularly, the invention relates to improved feminine hygiene kits designed for females during or for unexpected menstruation. These kits provide underwear, feminine wipes and a feminine sanitary towel.

Discussion of the Background

Fertile female humans and other female primates goes through a process called menstrual cycle. Menstrual cycle is a cycle that occurs in the uterus and ovary for the purpose of sexual reproduction. One of the steps during the menstrual cycle is call menstruation. Menstruation is a periodic discharge of blood and some mucosal tissue from the uterus and vagina. Usually during this period the females wears a feminine sanitary towel or any absorbent item outside the vaginal area in order to absorb the blood and some mucosal tissue without damaging the female underwear.

However females, more often younger females cannot predict the exact date when they are going to have their periods. Dealing with an unexpected menstruation can be tough and uncomfortable. Sometime the period even start during typically daily events. Mainly during the unexpected period underwear is damaged by blood. Therefore there is a need to provide a kit, easy to carry, that offers a greater degree of discretion, convenience, and portability to females.

SUMMARY

The present invention relates to the packaging and dispensing of a female care product, and in particular to a feminine hygiene kit that offers a greater degree of discretion, convenience, and portability to consumers during the event of unexpected periods.

In general, the present disclosure overcomes the disadvantages and shortcomings of prior art by disclosing feminine hygiene kit comprising at least underwear, at least a feminine wipes and at least a feminine sanitary towel.

In one embodiment, the feminine hygiene kit includes a shaped base, compacted underwear, a feminine wipe and at least a feminine sanitary towel in an individual compacted sealed pouch.

Another object of this disclosure is to provide a feminine hygiene kit with basic item for the event of unexpected periods.

Another object of this disclosure is to provide a compact feminine hygiene kit easy to carry.

Still another object of the present disclosure is to provide a light weight feminine hygiene kit with basic items for the event of unexpected periods.

Yet another object of the present disclosure is to provide a feminine hygiene kit shaped for convenient handling of the product.

The disclosure itself, both as to its configuration and its mode of operation will be best understood, and additional objects and advantages thereof will become apparent, by the following detailed description of a preferred embodiment taken in conjunction with the accompanying drawings.

The Applicant hereby asserts, that the disclosure of the present application may include more than one invention, and, in the event that there is more than one invention, that these inventions may be patentable and non-obvious one with respect to the other.

Further, the purpose of the accompanying abstract is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the disclosure of the application, which is measured by the claims, nor is it intended to be limiting as to the scope of the disclosure in any way.

BRIEF DESCRIPTION OF THE DRAWINGS

The accompanying drawings, which are incorporated herein, constitute part of the specification and illustrate the preferred embodiment of the disclosure.

DESCRIPTION OF THE PREFERRED EMBODIMENT

Figure 1:
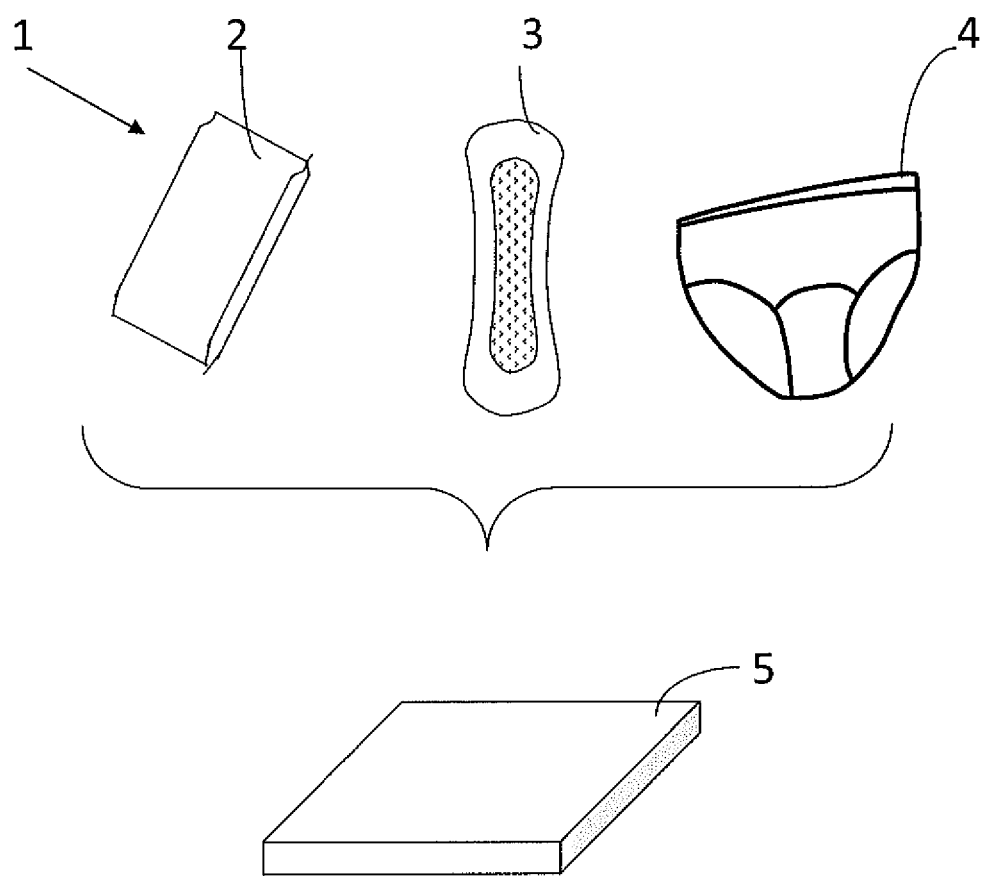
FIG. 1 shows a general structure in accordance with the principles of the present disclosure.

FIG. 1 shows a general structure in accordance with the principles of the present disclosure. The feminine hygiene kit 1 comprises at least a shaped base 5, at least underwear 4, at least sanitary towel 3, more particularly a feminine sanitary towel, and at least wipe 2.

Figure 2:
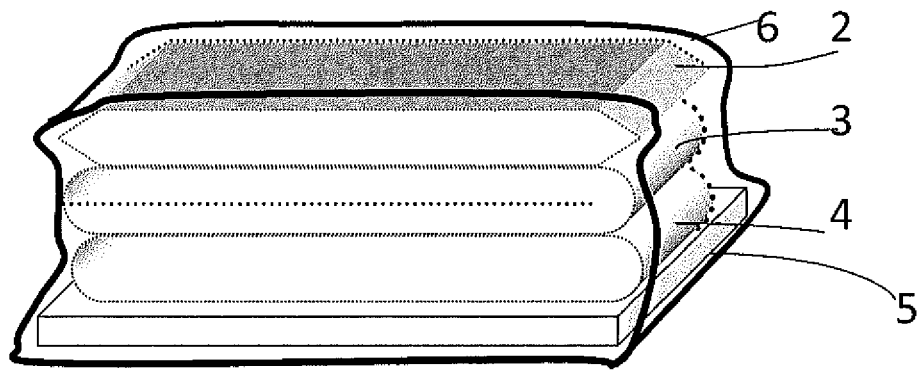
FIG. 2 shows a general structure of the feminine hygiene kit in accordance with the principles of the present disclosure.

Further the underwear 4, sanitary towel 3 and the wipe 2 are positioned on top of the rigid base 5 and emended in a transparent material 6 with shrinkage characteristics, as shown in FIG. 2.

As discussed above, the object of the present invention is to provide a compact light weigh feminine hygiene kit 1 comprising the basic items for the event of unexpected periods. The basic items comprise, as mentioned before, an underwear, a sanitary towel and a feminine wipe. The underwear, more particularly the female underwear comprises a waistband, such as an elastic waistband, a crotch panel to cover the genital area and a pair of leg openings which. Different materials can be used, however compactable breathable material, such as cotton, is preferred. The sanitary towel is an absorbent item preferably made of a compactable absorbent material, such as cotton and hemp. The feminine wipes are cleansing cloths meant to clean the female genital area. The feminine wipe may include antibacterial properties, fragrance or any type of substance or medicine direct to female genital area.

Figure 3:
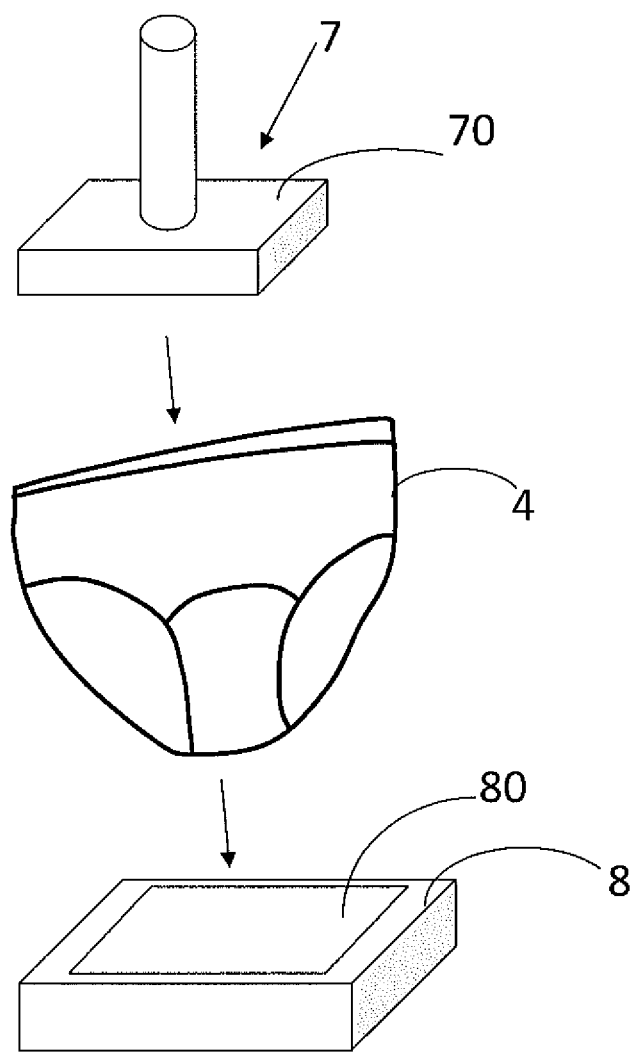
FIG. 3 shows a general structure of the compression cycle for the underwear in accordance with the principles of the present disclosure.

FIG. 3 shows a general structure of the compression cycle for the underwear. The process of compression comprises a compressing machine, wherein said compressing machine comprises a mold 8 and a pressing arm 7. The mold 8 is placed directly below the pressing arm 7. The mold 8 is fixed to a surface in such way it does not move during the pressing process. Further after ensuring the mold is placed and firm at the surface, the female underwear 4 is placed inside the mold at a shaped cavity 80. In the instant case the cavity 80 is configured to have the shape similar to the shaped base 5. Before pressing the underwear material is well distributed in the mold 8 inside cavity 80. Then we placed the compressing plate 70 above the underwear which is inside the mold's cavity 80. The compressing plate 70 is configured to travel inside the cavity in such way that compresses the underwear between the compressing plate 70 and the cavity 80 bottom surface. The underwear 4 is compressed for several seconds at maximum pressure. After a first compression cycle the compression plate 70 is removed.

Figure 4:
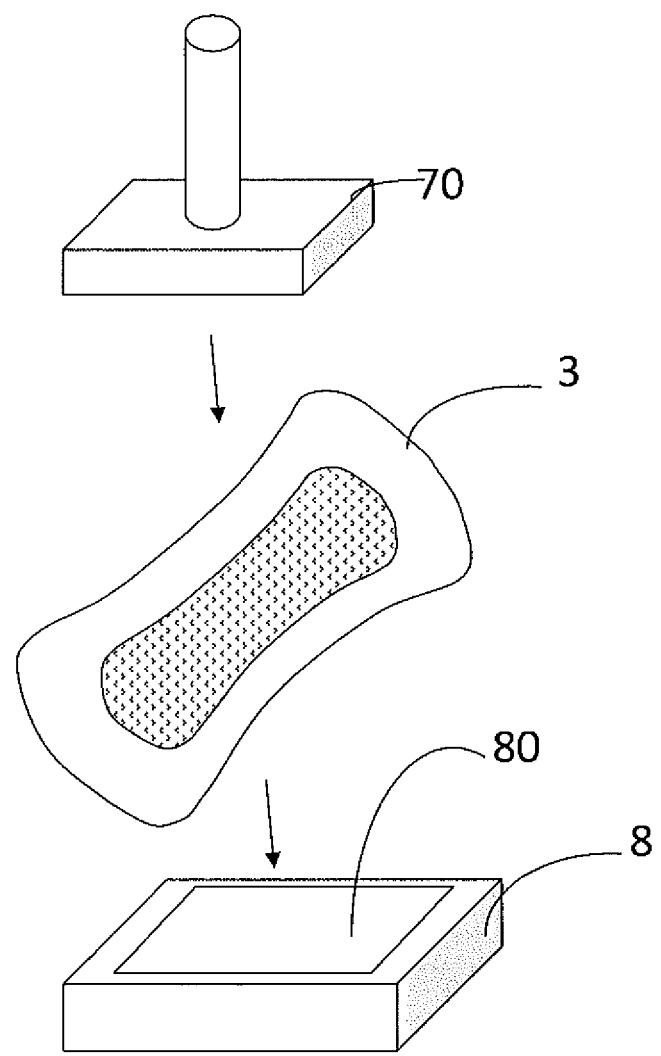
FIG. 4 shows a flowchart exemplary embodiment of the compression cycle for the feminine sanitary towel in accordance with the principles of the present disclosure.

After removing the compression plate 70 the sanitary towel 3, as shown in FIG. 4, is placed inside cavity 80. The sanitary towel 3 is folded to fit inside cavity 80. It is important to understand that the compacted underwear still inside cavity 80 while the sanitary towel 3 is positioned on top inside the cavity 80. Once the sanitary towel 3 is well placed inside the cavity the sanitary towel 3 is compressed. In the instant case, the sanitary towel 3 is compressed with less pressure for several seconds when compared to the first cycle. One of the reasons is to avoid damages to the pre-fabricated sanitary towel 3. After the compression of the underwear 4 in combination with the sanitary towel 3 is performed the second cycle is completed. When the second cycle of compression is finished the compressed material, including the underwear 4 in combination with the sanitary towel 3, is removed from the mold 8 for the packing process.

Figure 5A:
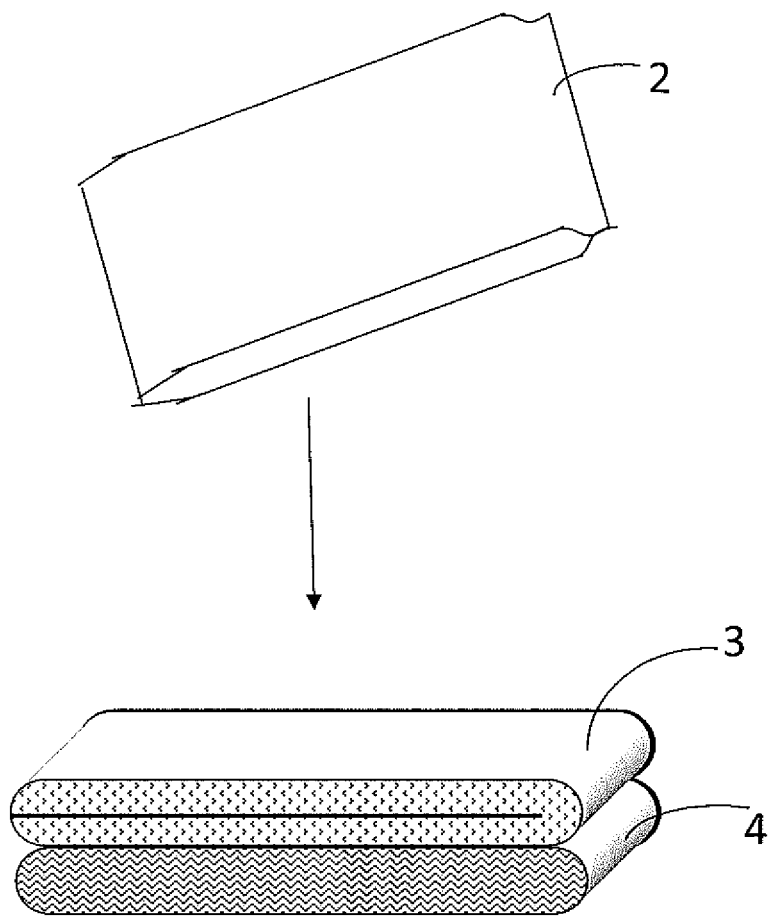
FIGS. 5A-5B shows a first exemplary embodiment of the underwear, feminine sanitary towel and feminine wipe assembly in accordance with the principles of the present disclosure.
Figure 5B:
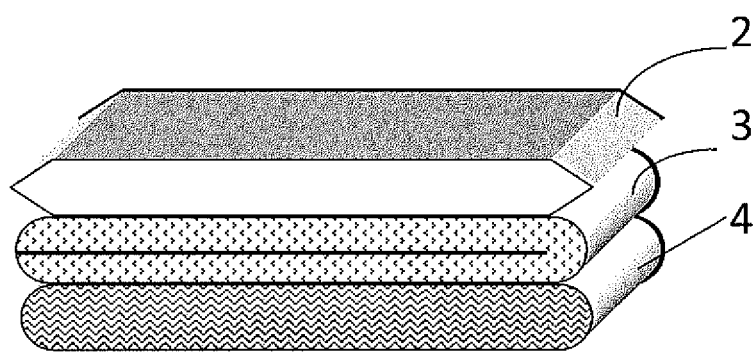

FIGS. 5A-5B shows a first exemplary embodiment of the underwear, feminine sanitary towel and feminine wipe assembly as part of packing process in accordance with the principles of the present disclosure. The feminine wipe 2 is placed on top or at the bottom of the compacted underwear 4 and compacted sanitary towel 3. The assembly of the compacted underwear 4 and compacted sanitary towel 3 and feminine wipe 2 is the result of the basic items.

Figure 6:
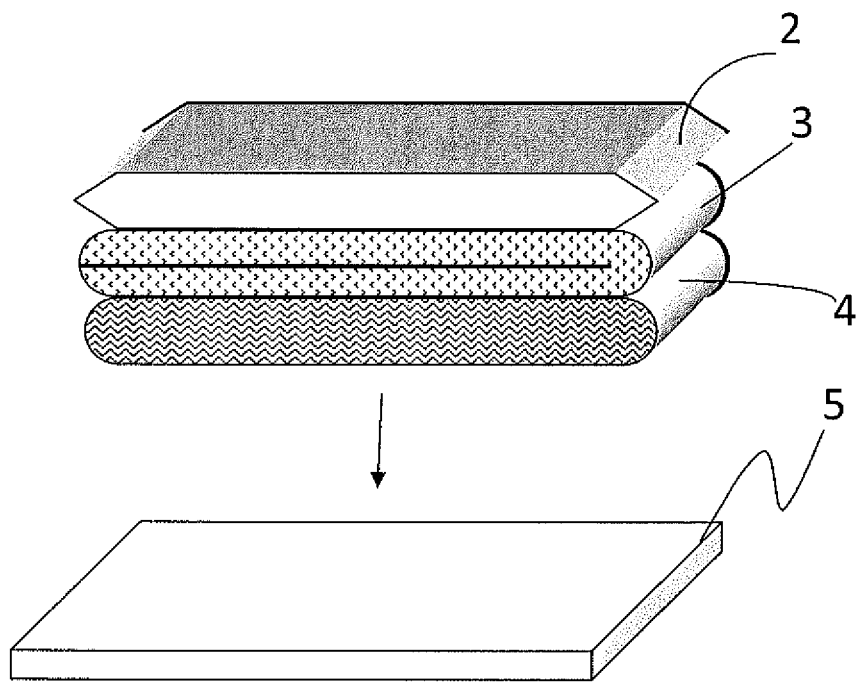
FIG. 6 shows a first exemplary embodiment of the underwear, feminine sanitary towel, feminine wipe and shaped base in accordance with the principles of the present disclosure.

Further the basic items are positioned over the shaped base 5, as shown in FIG. 6. As mentioned the compacted underwear and compacted sanitary towel 3 is configured to comprise a shape similar or smaller to shaped base 5 perimeters in such way that do not exceed the shaped base perimeter once it is located on top of the shaped base 5. For example, in the instant case the compacted underwear 4 and compacted sanitary towel 3 comprises a square shape similar to shaped base 5 not exceeding the shaped base perimeters once each piece is located on top of the shaped base 5. The shaped base 5 comprises a rigid body providing stability to the feminine hygiene kit 1.

Figure 7:
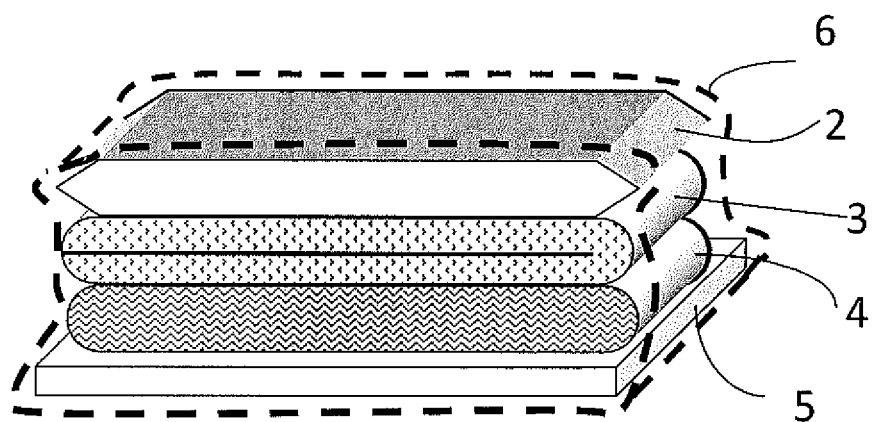
FIG. 7 shows a first exemplary embodiment of the underwear, feminine sanitary towel, feminine wipe and shaped base in accordance with the principles of the present disclosure.

After the basic items 2,3,4 and shaped base 5 are aligned and placed together said assembly is covered with a heat-shrinkable material, as shown in FIG. 7. The heat-shrinkable material 6 is preferred to be transparent and with shrinkable characteristics when heat is applied. In the instant case once the assembly is covered with the heat-shrinkable material 6 heat is applied in order to seal the package including the basic items 2,3,4 and shaped base 5. The heat may be applied using an oven or a heat blower gun or any other device of providing heat regulation capability.

Figure 8:
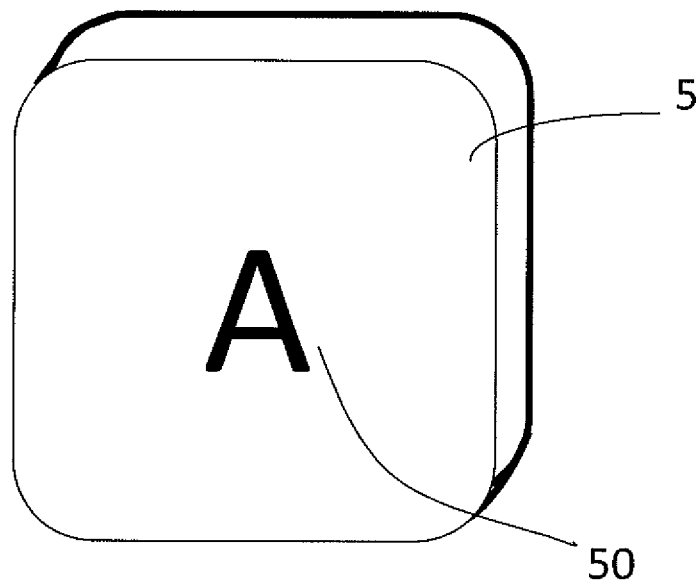
FIG. 8 shows a first exemplary embodiment of the compacted underwear, compacted feminine sanitary towel, feminine wipe and shaped base embedded in a bag of transparent and shrinkage characteristics in accordance with the principles of the present disclosure.

As mentioned the shrinkable material 6 is preferred to be transparent in order to use the shaped base 5 as a promotional means. A display 50 may be included as part of the back part of the shaped base 5, which is the part not covered by the basic items, as shown in FIG. 8. Several designs or any visual form of communication for marketing may be located at the display 50.

The disclosure is not limited to the precise configuration described above. While the disclosure has been described as having a preferred design, it is understood that many changes, modifications, variations and other uses and applications of the subject disclosure will, however, become apparent to those skilled in the art without materially departing from the novel teachings and advantages of this disclosure after considering this specification together with the accompanying drawings. Accordingly, all such changes, modifications, variations and other uses and applications which do not depart from the spirit and scope of the disclosure are deemed to be covered by this disclosure as defined in the following claims and their legal equivalents. In the claims, means-plus-function clauses, if any, are intended to cover the structures described herein as performing the recited function and not only structural equivalents but also equivalent structures.

All of the patents, patent applications, and publications recited herein, and in the Declaration attached hereto, if any, are hereby incorporated by reference as if set forth in their entirety herein. All, or substantially all, the components disclosed in such patents may be used in the embodiments of the present disclosure, as well as equivalents thereof. The details in the patents, patent applications, and publications incorporated by reference herein may be considered to be incorporable at applicant's option, into the claims during prosecution as further limitations in the claims to patently distinguish any amended claims from any applied prior art.

The invention claimed is:

1. A hygiene kit comprising:
    an individual compacted sealed pouch;
        a shaped rigid base, wherein said shaped rigid base comprises a top surface,
        at least a compacted underwear comprising a first material, wherein said first material is compressed to form a first compressed material,
        at least a compacted wipe,
        at least a compacted pre-fabricated sanitary towel comprising a second material, wherein said second material is compressed on top of said first material to form a second compressed material, wherein said first material is different from said second material;
    wherein said at least compacted underwear, said at least compacted wipe and said at least compacted sanitary towel are-positioned and vertically aligned on top of the top surface; wherein the compacted underwear comprising the first material is located between the shaped rigid base and said second material; and wherein said at least compacted underwear, said at least compacted wipe and said at least compacted sanitary towel and said shaped rigid based are embedded in said individual compacted sealed pouch; wherein said individual compacted sealed pouch comprises a shrinkable material, wherein said shrinkable material shrinks and seals said at least compacted underwear, said at least compacted wipe and said at least compacted sanitary towel and said shaped rigid base inside said individual compacted sealed pouch.

2. The hygiene kit of claim 1, wherein said compacted underwear is configured not to exceed the shaped rigid base perimeter when said compacted underwear is on top of the top surface.

3. The hygiene kit of claim 1, wherein said compacted sanitary towel is configured not to exceed the shaped base perimeter when said compacted sanitary towel is on top of the shaped base.

4. The hygiene kit of claim 1, wherein said shrinkable material is a heat shrinkable material.

5. The hygiene kit of claim 1, wherein said wipe comprises a fragrance.

6. The hygiene kit of claim 1, wherein said shrinkable material comprises a transparent shrinkable material.

* * * * *